(12) United States Patent
Bakhtyari-Nejad-Esfahani (10) Patent No.: US 10,993,738 B2
(45) Date of Patent: May 4, 2021

(54) NEEDLE LOCATION DEVICE

(71) Applicant: Olberon Medical Innovation SAS, Loos (FR)

(72) Inventor: Arash Bakhtyari-Nejad-Esfahani, Nottingham (GB)

(73) Assignee: Olberon Limited, Nottingham (GB)

(*) Notice: Subject to any disclaimer, the term of this patent is extended or adjusted under 35 U.S.C. 154(b) by 591 days.

(21) Appl. No.: 14/764,819

(22) PCT Filed: Feb. 3, 2014

(86) PCT No.: PCT/EP2014/052069
§ 371 (c)(1),
(2) Date: Jul. 30, 2015

(87) PCT Pub. No.: WO2014/118376
PCT Pub. Date: Aug. 7, 2014

(65) Prior Publication Data
US 2015/0359560 A1    Dec. 17, 2015

(30) Foreign Application Priority Data

Feb. 1, 2013  (GB) .................................. 1301866

(51) Int. Cl.
*A61B 17/34* (2006.01)
*A61B 10/02* (2006.01)
(Continued)

(52) U.S. Cl.
CPC ........ *A61B 17/3403* (2013.01); *A61B 8/0841* (2013.01); *A61B 10/0275* (2013.01); *A61B 10/04* (2013.01); *A61B 2010/0208* (2013.01); *A61B 2010/045* (2013.01); *A61B 2017/3413* (2013.01); *A61B 2090/3929* (2016.02)

(58) Field of Classification Search
CPC .................... A61B 17/3403; A61B 2010/0208
See application file for complete search history.

(56) References Cited

U.S. PATENT DOCUMENTS

| 4,924,878 A | 5/1990 | Nottke |
| 4,944,308 A | 7/1990 | Åkerfeldt |

(Continued)

FOREIGN PATENT DOCUMENTS

| CN | 201179084 Y | 1/2009 |
| EP | 0453251 A1 | 10/1991 |

(Continued)

OTHER PUBLICATIONS

International Search Report and Written Opinion PCT/EP2014/052069 dated Oct. 4, 2014.

(Continued)

*Primary Examiner* — Sean P Dougherty
(74) *Attorney, Agent, or Firm* — Knobbe, Martens, Olson & Bear, LLP (57) ABSTRACT

A medical needle location device (10) is disclosed. The device (10) has a housing (12) arranged to be gripped by a user and a needle (20) supported by the housing (12). The needle (20) depends from the housing (12) towards a needle tip (14B). The housing (12) comprises an excitation mechanism (28) for applying an oscillatory motion to the needle (20) during location within the body.

21 Claims, 10 Drawing Sheets

(51) Int. Cl.
*A61B 8/08* (2006.01)
*A61B 10/04* (2006.01)
*A61B 90/00* (2016.01)

(56) References Cited

U.S. PATENT DOCUMENTS

| | | | |
|---|---|---|---|
| 5,538,010 A | 7/1996 | Darr et al. | |
| 5,967,991 A | 10/1999 | Gardineer et al. | |
| 6,048,321 A * | 4/2000 | McPherson | A61B 10/0233 600/564 |
| 7,008,383 B1 * | 3/2006 | Damadian | A61B 10/0233 600/567 |
| 2002/0183742 A1 | 12/2002 | Carmel et al. | |
| 2005/0165328 A1 * | 7/2005 | Heske | A61B 10/0275 600/566 |
| 2007/0032741 A1 | 2/2007 | Hibner et al. | |
| 2009/0118641 A1 * | 5/2009 | Van Dam | A61B 10/0266 600/567 |
| 2010/0160817 A1 * | 6/2010 | Parihar | A61B 10/0275 600/565 |
| 2012/0130414 A1 | 5/2012 | Birkill et al. | |
| 2012/0209303 A1 * | 8/2012 | Frankhouser | A61B 10/025 606/169 |
| 2014/0026693 A1 * | 1/2014 | Eller | F16H 19/043 74/30 |

FOREIGN PATENT DOCUMENTS

| | | |
|---|---|---|
| EP | 2679188 A1 | 1/2014 |
| GB | 2367895 A | 4/2002 |
| WO | WO 2008024684 A2 | 2/2008 |
| WO | WO 2014118376 A1 | 8/2014 |

OTHER PUBLICATIONS

GB Search Report issued for corresponding Great Britain Patent Application No. GB1301866.8, dated Dec. 5, 2013.
International Preliminary Report on Patentability in regard to PCT/EP2014/052069 dated Aug. 4, 2015 in 6 pages.

* cited by examiner

NEEDLE LOCATION DEVICE

The present invention concerns a medical needle location device to facilitate correct positioning of a needle within a patient's body and more particularly, although not exclusively, to a biopsy needle device.

Percutaneous biopsy needle devices typically comprise a needle mounted within a sleeve for insertion into the body to take a tissue sample.

U.S. Pat. No. 4,924,878 discloses an example of such a device, in which a trigger mechanism is provided for selective actuation of the needle and sleeve at separate times. In this manner the device can first be primed and, once the needle is correctly cited, the needle can be released so that it projects beyond the sleeve. The needle has a tissue-receiving recess towards its tip, which is exposed by actuation of the needle. The sleeve is then released so that it moves relative to the needle and covers the recess, thereby trapping the tissue sample therein. The needle-and-sleeve assembly is then retracted to remove the tissue sample from the body.

Other examples of such manual spring-loaded trigger mechanisms for driving the sequential motion of the needle and sleeve to take a sample are described in U.S. Pat. Nos. 5,538,010 and 4,944,308.

WO 2008/024684 discloses a biopsy handset having a power source and an electric drive for driving relative motion between the needle and sleeve to take a sample in a manner similar to that described above. A rotational and/or linear driving motion between the needle and sleeve may be used to cut the sample. WO 2008/024684 also discloses the use of an electrically-powered pump in the handset to apply a vacuum force to the sample recess in the needle during sample taking.

The prior art described above focuses on the provision of actuation mechanisms to take a sample at the desired site in the body. However it has been found that the correct locating of the needle by physicians in order to take the desired sample can be difficult. In this regard, the physician is required to manually guide the needle tip to the desired site and retain the tip accurately in place whilst the tissue sample is taken. If the needle is not held at the desired site during triggering of the device, an incorrect sample may be taken. Repeated relocation of the needle and/or re-taking of samples can cause discomfort and distress to a patient.

It is known to use ultrasound imaging to help the physician guide the biopsy needle to the intended site. However the different echogenicity of different tissue regions or cavities in the body can lead to difficulties in visualizing the needle. For example a fluid-filled cavity or duct will typically be black on screen when using ultrasound since it is anechoic or hypoechoic relative to surrounding tissue. In contrast, fat is hyperechoic in nature and will appear significantly lighter.

Thus as the needle passes through fat or hyperechoic tissue, it can be difficult to locate on screen. This is a particular problem for biopsy needles which are intended to be located in a desired tissue rather than within a fluid-filled cavity. Accordingly, even using ultrasound, it has been found that the correct locating of a biopsy needle can be problematic.

It is an aim of the present invention to provide a needle insertion device, which can be more accurately and/or consistently located, particularly when using ultrasound.

According to the present invention there is provided a medical needle location device comprising a housing arranged to be gripped by a user and a needle supported by the housing, the needle depending from the housing towards a needle tip, wherein the housing comprises an actuation mechanism for applying an oscillatory motion to the needle during location within the body.

The actuation mechanism may comprise an excitation mechanism. The actuation mechanism may be arranged to cause excitation of the needle for a duration of 1 second or more. Typically the duration of excitation is a plurality of seconds.

The actuation mechanism may comprise a vibration-inducing mechanism.

It has been found that the excitation of the needle during insertion causes the echogenicity of the needle relative to surrounding tissue to be altered, thereby allowing the needle to be clearly viewed on an ultrasound display. Furthermore the excitation of the needle, as opposed to gross longitudinal or lateral movement of the needle, has been found to have little negative impact on the accuracy of needle positioning.

It has also been found that the excitation of the needle may advantageously be communicated to the surrounding tissue and may improve ultrasound imaging thereof.

The actuation mechanism may also comprise a drive mechanism. The drive mechanism may drive the excitation mechanism. The drive mechanism may transfer energy to the excitation mechanism, eg by causing movement of the excitation mechanism. The drive mechanism may determine the frequency and/or magnitude of the oscillatory motion applied to the needle.

The oscillatory motion may have a frequency in the region of 5-50 Hz. The oscillatory motion most preferably has a frequency in the region of 30 Hz.

The drive mechanism may comprise a user interface portion, and may be powered or primed by manual movement of the user interface portion. The user interface portion may comprise a graspable member. The user interface portion may take the form of a handle, trigger, arm, lever, or the like. The user interface portion may actuate the drive mechanism and/or may provide energy to the drive mechanism.

The user interface portion may be actuatable by a user. The user interface portion may be moveable by a user. The movement of the user interface portion may be longitudinal, rotational, pivotal, or any other appropriate type of movement. The user interface portion may be moveable relative to the housing of the device. The user interface portion may be moveable towards a portion of the housing of the device during actuation, eg in the form of a trigger or the like. Such an arrangement may allow the actuation mechanism to be operated with one hand, thereby increasing the ease of operation of the device. Alternatively, the user interface portion may be moveable away from a portion of the housing of the device during actuation, although this arrangement may require two hands for operation of the actuation mechanism.

The drive mechanism may comprise a return mechanism. The return mechanism may resiliently bias the user interface portion into a rest configuration relative to the housing. The return mechanism may act to return the drive mechanism to a rest configuration once the user interface portion has been actuated by a user. The return mechanism may take the form of a spring or the like.

The actuation mechanism may comprise at least one excitation member, which may be a rotatable member. The rotatable member may be arranged to impart a cyclical excitation force to the needle at a frequency dependent on the rotational speed of the rotatable member. The rotatable member may be arranged to impart a linear excitation force to the needle. The rotatable member may be arranged to impart a force to the needle along at least one axis, eg a longitudinal axis of the needle. The rotatable member may be arranged to impart forces to the needle in a plurality of directions, eg in substantially one plane. The rotatable member may comprise an eccentric (i.e. may have unevenly distributed mass in the direction of rotation about an axis). Additionally or alternatively, the rotatable member may comprise one or more projections arranged to impact with a receiving member. Additionally or alternatively, the rotatable member may comprise a toothed wheel or cam.

An intermediate member may be provided in the force path between the excitation member and the needle. The intermediate member may comprise a transfer component, as defined below.

The drive mechanism may cause movement of the excitation mechanism, eg the excitation member or an intermediate member. The movement of the excitation mechanism may be rotational. The movement of the excitation mechanism may be confined to one plane. The drive mechanism may comprise a plurality of gears. The plurality of gears may provide an increased level of torque and/or speed of rotation to the excitation mechanism.

The drive mechanism may comprise a drive member. The drive member may engage the excitation mechanism, eg the excitation member and/or an intermediate member, and may cause motion thereof. The drive member may releasably engage the excitation mechanism. The drive member may comprise a portion shaped to engage a corresponding portion of the excitation mechanism.

The drive member may be actuable between a first configuration in which the drive member is engaged with the excitation mechanism, and a second configuration in which the drive member is disengaged from the excitation mechanism. The first configuration may correspond to a period when the drive mechanism, eg the user interface portion, is operative, eg energy is being effectively transferred to the excitation mechanism, and the second configuration may correspond to a period when the drive mechanism is inoperative, eg energy is not being effectively transferred to the excitation mechanism. The drive mechanism may comprise a release mechanism. The release mechanism may be triggered by any one of a number of different parameters that at least approximate to the end of effective energy transfer to the excitation mechanism, including a predetermined position of the user interface portion, eg during actuation, a predetermined time period, eg since actuation, and a signal from an energy store, for example.

The release mechanism may comprise a resilient member, eg a spring or the like, that is engaged with the drive member. The resilient member may be deformable from a rest configuration into the first configuration. Thus the drive member may be resiliently biased when it is in the first configuration. The resilient member may act to move the drive member from the first configuration to the second configuration.

The drive member may be configured so as to engage the excitation mechanism for a limited period of time only. The drive member may be advanced into the first configuration upon movement of the user interface portion by a user during actuation. Further movement of the user interface portion by a user may advance the drive member from the first configuration to the second configuration.

The excitation mechanism may be configured to maintain its motion when the drive mechanism is in the second configuration.

The excitation mechanism and/or the excitation member may be mounted independently of the drive mechanism. The excitation mechanism and/or the excitation member may be rotatably mounted relative to the drive mechanism.

The excitation member may be coupled to the needle, eg by a transfer component, such that movement of the excitation member in one or more axes, relative to the device housing, causes corresponding movement of the needle. The transfer component may comprise a housing for at least part of the needle. The excitation member and the needle may be fixed relative to each other, such that these components are rigidly coupled, for example, or these components may be arranged to allow relative movement between the excitation member and the needle in at least one axis.

Where the excitation member is rotatable, the needle may be coupled to the excitation member by a mechanism including a transfer component, the transfer component being moved in a substantially reciprocating motion by the excitation member. This may be achieved by the excitation member and/or the transfer component having the form of a cam mechanism, eg a cam mounted to the rotatable excitation member engaged with a track of the transfer component.

The transfer component may be mounted for substantially reciprocating motion, eg slidably mounted, relative to the device housing along a principal axis, and may be mounted to allow further motion in one or more orthogonal axes, eg to a lesser degree. This further motion may be achieved by providing at least some play in the slidable mounting. The principal axis may be substantially parallel to the longitudinal axis of the needle.

In one embodiment, the actuation mechanism may comprise an impact mechanism. The impact mechanism may be arranged to convert an input force into one or a plurality of impacts. The impact force may be transmitted to the needle by a receiver or intermediate member. Alternatively, an impact member may act on a portion of the needle. The impact member may be a pivoting member.

The actuation mechanism may excite a portion of the needle spaced from the tip, for example a portion of the needle held within the housing. Excitation is thus communicated along the length of the needle to the tip. The needle may be held at one end within the housing, for example in a manner which promotes reflection of vibrations along the needle towards the tip.

The drive mechanism may be adapted to receive energy input from a user, eg by means of the moveable user interface portion, eg the graspable member, being coupled directly, or via intermediate members, to the drive mechanism. Alternatively, the drive mechanism may be adapted to receive energy from an energy store, which may be charged manually or electrically, for example.

The device may comprise an energy store, for example which may be located in the housing. The energy store may comprise a mechanical energy store, for example a spring. Additionally or alternatively, the energy store may comprise an electro-chemical energy store, such as a battery. Accordingly the actuation mechanism may be manually or electrically driven.

In the example of a mechanical energy store, the actuation mechanism may be manually actuated or primed. The device may comprise a lever, trigger, pull-bar, thumb-wheel or other manual input member. The input member may be, or may be in force communication with, a spring or other resiliently deformable member. The input member may move or deform the resiliently deformable member from an at-rest, or equilibrium, condition to an actuated condition.

The actuation mechanism may be arranged to resist the return of the resiliently deformable member to its at-rest condition.

The actuation mechanism is typically located within the housing. The needle may be detachable from the housing and/or actuation mechanism. A first portion of the housing in which the actuation mechanism is located may be detachable from a second portion of the housing, to which the needle may be mounted.

The term "needle" as used herein is intended to cover various different forms of elongate puncture device for insertion into the human or animal body, such as a stylet, obturator, trocar or similar.

The device may comprise a biopsy needle device. A sleeve may depend from the device and may be arranged about the needle. The needle and sleeve may be a close fit. Such a sleeve may be referred to as a sheath or cannula.

The actuation mechanism may comprise a first actuation mechanism. The device may comprise a second actuation mechanism for gross actuation of the needle and/or an associated sleeve. The second actuation mechanism may comprise a conventional biopsy needle trigger or deployment mechanism and may be manually or electrically powered. The second actuation mechanism may be maintained within the housing The housing may comprise a power source, such as a battery. A first portion of the housing comprising the needle may be detachable from a second portion of the housing, which may comprise the power source.

The housing, or a portion thereof, may be disposable.

Practicable embodiments of the invention are described in further detail below by way of example only with reference to the accompanying drawings, of which.

Figure 1:
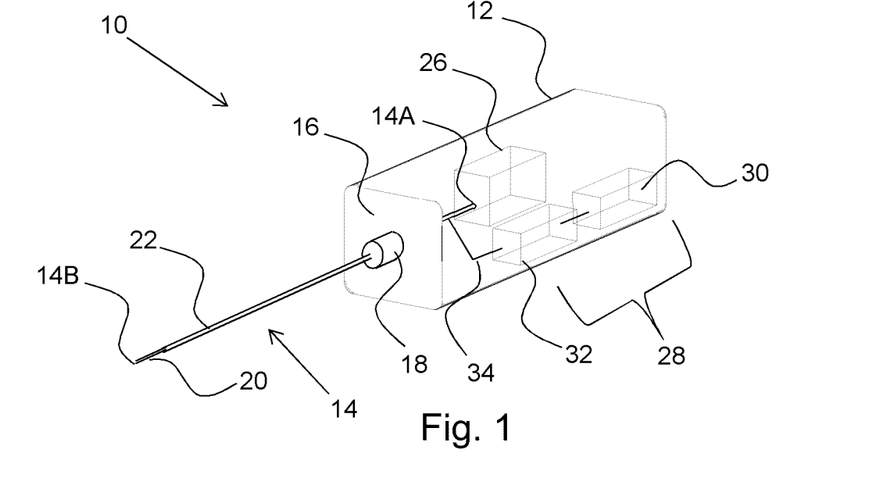
FIG. 1 shows a partially-transparent schematic three-dimensional view of a device according to one example of the present invention.

Turning firstly to FIG. 1, there is shown the general arrangement of a needle insertion device 10 according to one example of the invention. This example relates to a biopsy needle device for taking tissue samples from a patient but it will be appreciated that the principles of excitation described below and the various different mechanisms for exciting a needle may be implemented in other types medical needle devices, particularly if such devices are used in conjunction with ultrasound imaging equipment in order to allow needle visualisation when positioning the needle at the desired site within the body.

In FIG. 1, the device 10 comprises a housing 12 intended to be gripped by a user. The housing 12 is preferably substantially formed of a plastic material and provides an outer shell, within which the actuation mechanisms to be described below can be housed. Although not shown in the figures, the outer wall or casing of the housing may be ergonomically shaped so at to provide a comfortable and secure profile to be gripped by the user. Furthermore the housing may comprise one or more portions of a suitable polymer material to provide improved grip.

A needle assembly 14 protrudes from the housing. The needle assembly is elongate in form and extends from a proximal end 14A which is mounted within the housing 12 to a distal end or tip 14B, which is external of, and spaced from, the housing. The needle assembly may be supported part-way along its length by the housing wall 16 and/or a support formation 18 thereon, such as a needle holder arrangement. The needle assembly 14 passes through such a needle holder and a corresponding opening in the wall 16. The wall 16 may be a frontal wall of the housing 12.

The needle assembly 14 comprises an inner needle 20 and a sleeve 22 closely surrounding the needle. The needle assembly 14 may comprise a conventional biopsy needle assembly such that the needle 20 has a recess 24 (see FIG. 2) a short distance from the tip 14B. The needle 20 typically terminates at the tip in a bevel to provide a puncturing tip formation.

The needle 20 and sleeve 22 may be actuated in a conventional manner (e.g. sequentially, starting with the needle) for a biopsy needle assembly as described above with reference to the prior art for the purpose of taking a tissue sample. Accordingly such a mode of operation will not be described again here for brevity save to say that the needle can selectively project beyond the sleeve as required to expose the recess 24 and the sleeve can selectively cover the recess 24 to trap a tissue sample therein.

The actuation mechanism for obtaining a tissue sample is hereinafter referred to as a deployment mechanism 26 which provides a mechanism for triggering gross movement (e.g. longitudinal or rotational movement) of the needle and sleeve individually to trap a tissue sample in the recess 24. Any conventional deployment mechanism 26 known to the skilled person (either manually or electrically driven) may be used in conjunction with the present invention.

Also an actuation mechanism in accordance with the present invention is provided within the housing 12, which is hereinafter referred to as an excitation mechanism 28. The excitation mechanism 28 generally comprises an energy/force input mechanism 30 and a needle actuator 32. The input mechanism transmits a displacement force to the actuator 32, which in turn excites the needle for a period of time as will be described more fully with reference to the examples of FIGS. 2-6.

In this embodiment, the actuator transmits an excitation force to a portion of the needle assembly between the point of contact with deployment mechanism 26 and the housing wall. However in other embodiments, the actuator may transmit excitation to the needle at a location between the deployment mechanism and a distal end of the needle assembly as necessary. The actuator 32 may act directly on the needle assembly (e.g. the sleeve) or else may be connected thereto by an intermediate member or linkage 34.

In use the excitation mechanism 28 may be operated independently of the deployment mechanism 26. The excitation mechanism is intended to be operated when locating the needle by a physician.

Figure 2:
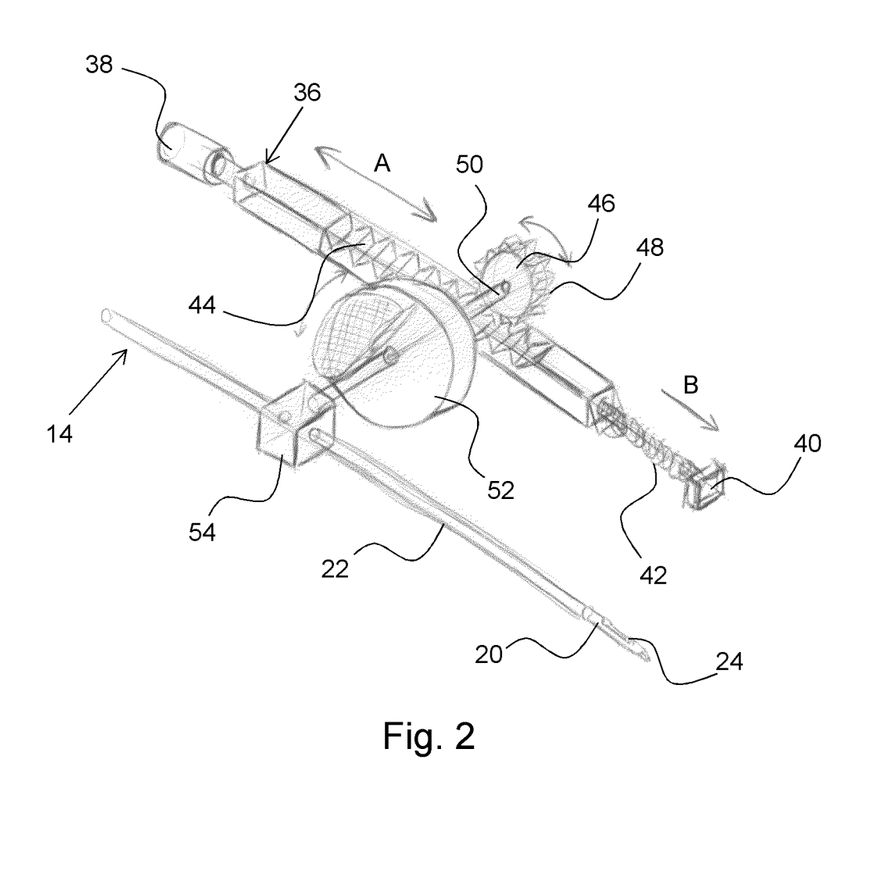
FIG. 2 shows a schematic three-dimensional view of an excitation mechanism according to one example of the invention.

In FIG. 2, there is shown a first example of an excitation mechanism. In this example, a manual input mechanism is provided in the form of a pull bar 36, which is mounted for linear movement in the direction of arrow A. The pull bar 36 has a handle portion 38, which protrudes to the exterior of the housing. The pull bar is connected to a fixed portion 40 of the housing via a coil spring 42. A series of teeth 44 are provided along the length of the pull bar.

A toothed wheel 46 (e.g. a gear wheel or pinion) is mounted such that the teeth 44 of the pull bar engage the teeth 48 on the wheel 46.

The wheel 46 is mounted for rotation on a shaft or axle 50. Accordingly the pull bar and wheel arrangement is akin to a rack and pinion mechanism.

The wheel shaft 50 is connected to a disk 52 having an unbalanced mass distribution, for example in the form of a counter-weight or eccentric. The shaft 50 passes through the disk 52 to a transfer block 54, within which the shaft can rotate. The needle assembly 14 passes through the transfer block, typically in a direction perpendicular to the direction of the shaft 50. The needle assembly is typically loosely held within the transfer block 54 part-way along its length such that the sleeve 22 and needle 20 can be deployed as required in use (e.g. by sliding in a longitudinal direction through the transfer block 54.

In use, the user pulls handle 38, thereby imparting tension in the coil spring 42 and priming the excitation mechanism. When the handle is released, the tension in the coil spring 42 pulls the pull bar 36 in the reverse direction, towards the fixed portion 40 (i.e. in the direction of arrow B). The meshing teeth of the bar and wheel thus cause rotation of the wheel 46, thereby rotating the disk 52 via shaft 50. The rotating eccentric causes vibration in the shaft 50 which is transmitted to the transfer block 54 and hence to the needle assembly.

Hence the needle assembly is vibrated for a period of time depending on the duration of rotation of the disk 52. This duration of excitation can be tailored as desired by setting any or any combination of: the length of displacement (including the length of the toothed section) of the pull bar 46; the resilience (e.g. spring constant) of the spring 42; and/or the resistance/inertia provided by the rotating wheel and shaft arrangement. In this manner the mechanism can be tailored to provide an ongoing vibration in excess of 1 or 2 seconds in duration, and preferably in the vicinity of 1-5 or 1-10 seconds duration. The mechanism may be tailored to provide relatively high frequency vibrations over a shorter period or relatively lower frequency vibrations over a longer period.

Also the shaft 50 can be split such that the wheel 46 drives the disk 52 in one direction only, thereby allowing the disk to free-wheel when the wheel 46 is stationary. If the disk 52 is provided with an inertia mass, this may allow the disk to rotate for extended periods of time thereby increasing the duration of vibrations experienced by the needle assembly.

Figure 3:
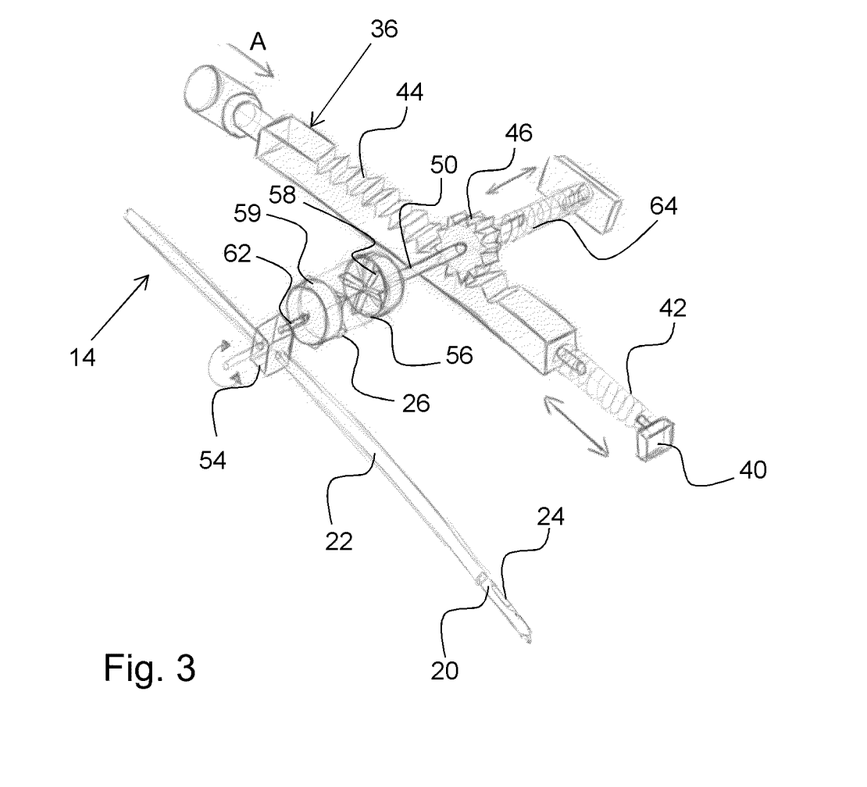
FIG. 3 shows a schematic three-dimensional view of an excitation mechanism according to a second example of the invention.

In FIG. 3 a further mechanism is shown in which the same pull-bar 36 and toothed wheel 46 arrangement is used as the input mechanism. Corresponding numerals are used for like features and will not be described again for brevity. In this example, unlike the example of FIG. 2, the toothed wheel 46 is connected to a different actuator 56 instead of eccentric 52. Shaft 50 connects the wheel 46 to the actuator 56, which takes the form of rotating member having one or more projections on a side wall or end face thereof. The actuator 56 may be disk-shaped.

An opposing receiver member 59 is typically static and may have one or more opposing projections 60. The receiving member 59 may be rigidly mounted to the housing and/or transfer block 54 by an intermediate arm 62 or other support member.

The projections 58 and/or 60 protrude from opposing faces of the rotating actuator 56 and receiver 59 and are angularly spaced, typically about a common axis, which may be the axis of rotation of the actuator 56. The rotating actuator 56 and receiver 59 are held such that the projections interfere.

In use when the wheel 46 is rotated by the input mechanism, the projections 58 on the actuator contact the projections of the receiver 60. The projections are angled or curved in profile such that the projections ride over each other, thereby allowing the actuator 58 to continue rotation, whilst the contact between the projections causes vibrations.

The vibrations generated by contact between the actuator 56 and receiver 59 are communicated to the transfer block 54 by intermediate member 62 and thus to the needle assembly 14.

The frequency of vibrations is a function of the rotational speed of the actuator 58 and the number of projections provided on the actuator and/or receiver. Thus the number of contacts between the projections per revolution can be altered to achieve a desired vibrational frequency in the needle assembly. This can be tailored in conjunction with the variables described in relation to FIG. 2 to vary the vibration behaviour and duration of the mechanism. Also the pull bar arrangement may move back and forth under the action of spring 42 to extend the period of vibration.

A biasing arrangement may be used to ensure adequate contact between the actuator 56 and receiver 59. A spring 64 or other suitable biasing means may be used for this purpose in order to apply a gentle compression force between the actuator 56 and receiver 59. The biasing means is also resilient to allow the projections 58 to ride easily over projections 60 without too large a resistance to rotation which would serve to dampen rotation of the actuator.

Figure 4:
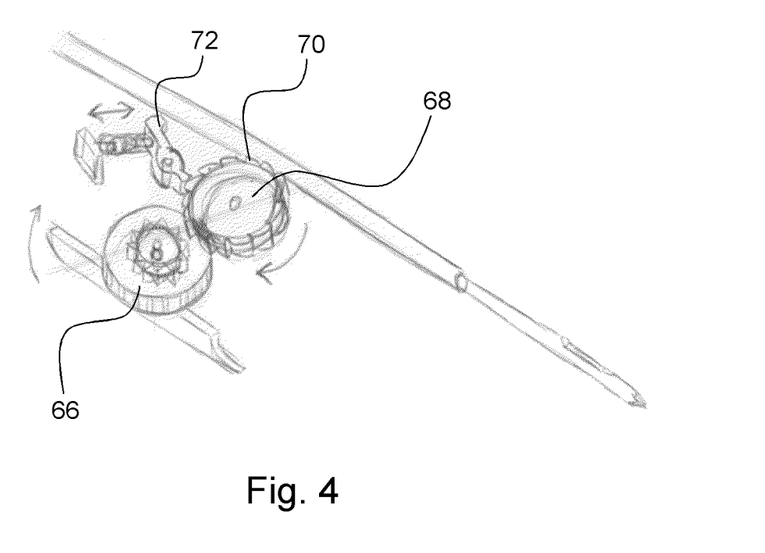
FIG. 4 shows a schematic three-dimensional view of an excitation mechanism according to a third example of the invention.

In FIG. 4, a different type of input mechanism and actuator are provided. A scroll wheel 66 or other rotational input means is provided in this embodiment to allow an input torque to be transmitted to the actuator. The scroll wheel is mounted in a torques transferring relations ship with a rotatable actuator wheel 68. The actuator has a series of teeth-like projections 70 distributed about its axis of rotation. In the example of FIG. 4, the teeth are provided on a circumferential edge in the manner of a ratchet wheel but could otherwise be provided on a side or end face of the actuator 68.

Either the scroll wheel or actuator may be mounted with respect to an energy storage means such as a coil spring or similar. The torque applied by manually turning the scroll wheel (e.g. by an operator's thumb or finger) may thus serve as a wind-up mechanism and the energy may be stored by the torque spring so as to drive rotation of the actuator 68.

An intermediate member in the form of a lever arm 72 is held in contact with both the teeth 70 of actuator 68 and the needle assembly (or a transfer block of the kind described above). The arm 72 may be resiliently mounted such that it is biased into contact with the teeth 70 but can be resiliently dislodged thereby. Rotation of the actuator thus causes a reciprocal movement of the arm 72 such that it repeatedly knocks against the needle assembly, thereby imparting vibrations in the needle assembly for the period of rotation of the actuator 68.

Figure 5:
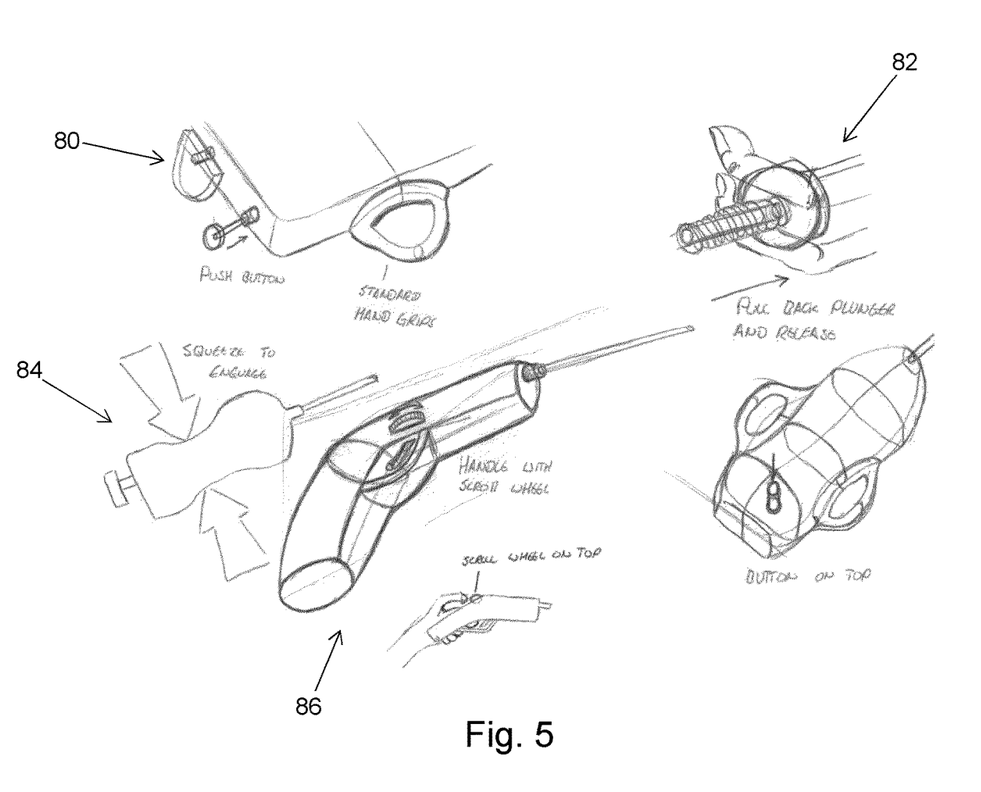
FIG. 5 shows various examples of input mechanisms for differing examples of manually actuated examples of the invention.

Whilst some of the above input mechanisms are described by way of example to a pull-bar input, it will be appreciated that the mechanisms may all operate in reverse by depressing a input member to compress a spring or other energy storage means instead of acting in tension. Furthermore it is envisaged that a variety of different input mechanisms may be employed to provide a required displacement of an actuator in order to generate the desired vibrations. Various examples are shown in FIG. 5 as follows:

- A push button arrangement 80 in an end of the device acting in compression
- A spring-loader plunger 82 acting in tension
- A resiliently deformable housing portion 84 which can be squeezed to deform the housing or a resilient member therein
- A scroll wheel 86, typically located for actuation by a user's thumb of finger
- A push button 88 in a major surface of the device, such as an upper surface of the housing Furthermore the input mechanism may be derived from a conventional input mechanism for deployment of the biopsy needle or sleeve. Thus a single manual input mechanism for the priming of a biopsy needle device may prime both the deployment mechanism and also the excitation mechanism by way of a single manual input action. Suitable independent latching arrangements for the deployment and excitation mechanisms can allow the excitation and deployment mechanisms to be triggered independently as required by the user.

Figure 6:
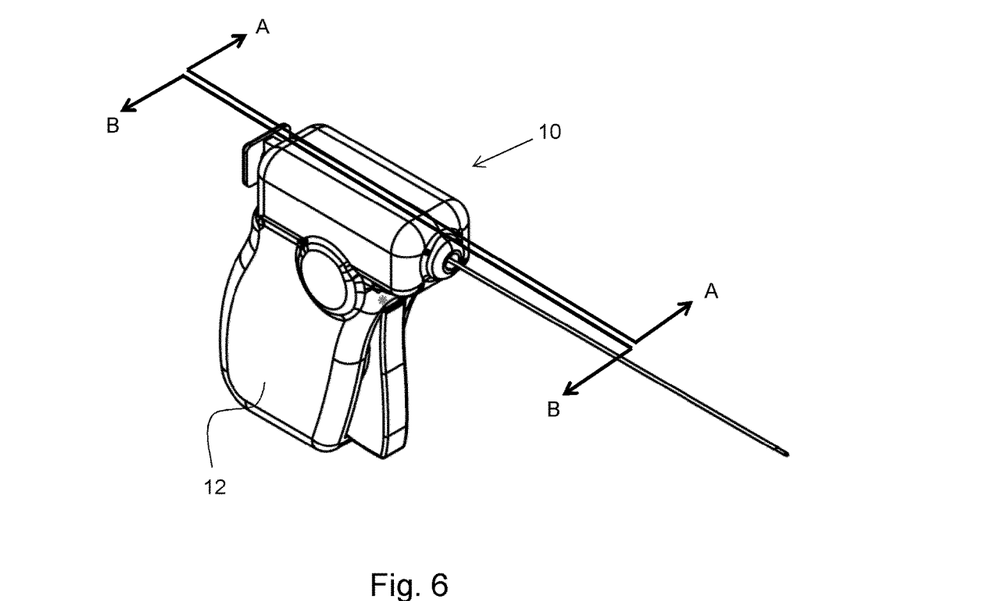
FIG. 6 shows a three-dimensional view of a device according to a preferred embodiment of the present invention.
Figure 7:
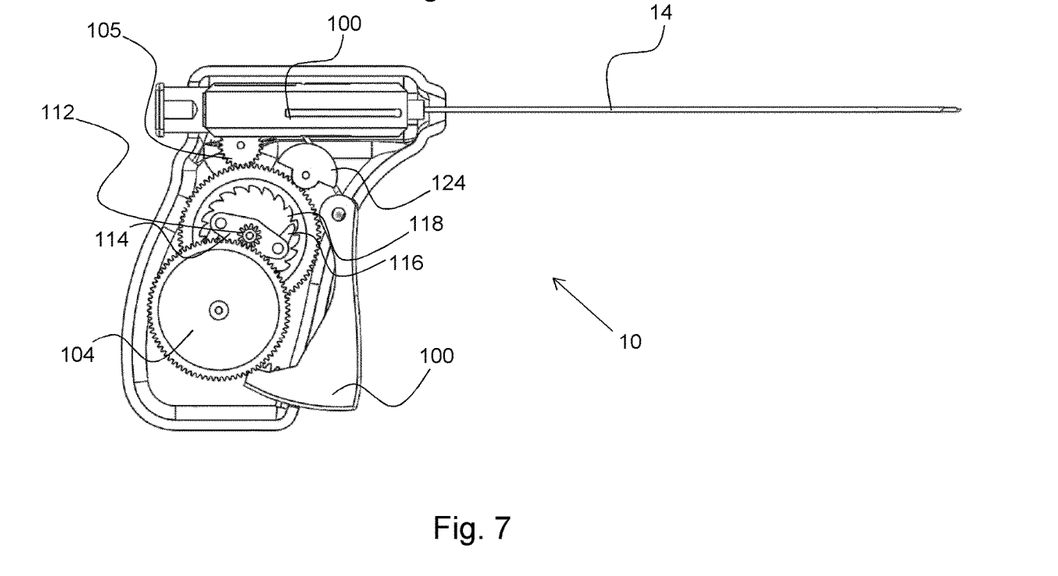
FIG. 7 is a sectional view along the line A-A shown in FIG. 6.
Figure 8:
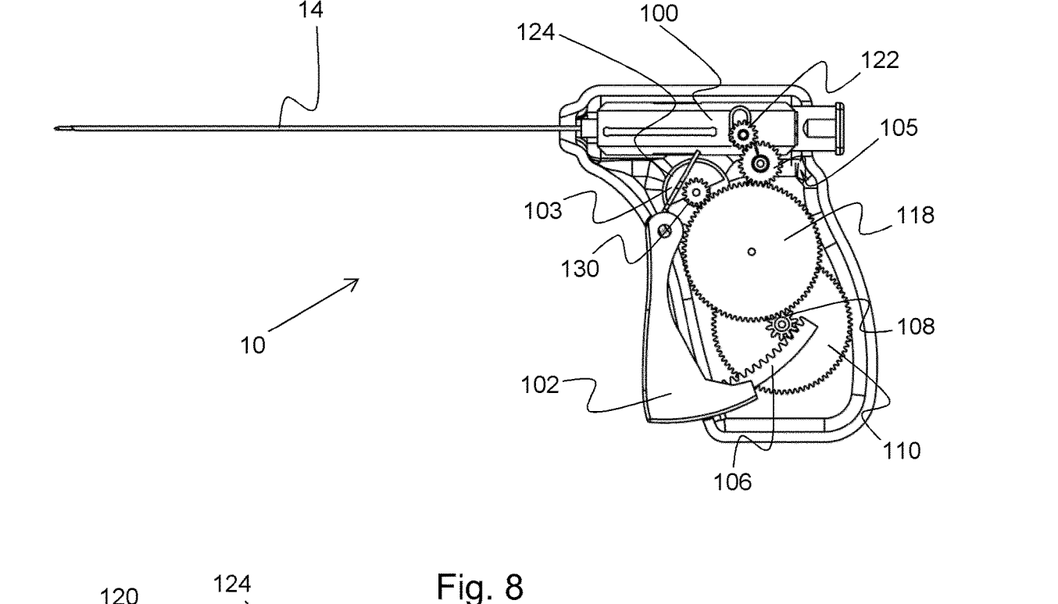
FIG. 8 is a sectional view along the line B-B shown in FIG. 6.

A preferred embodiment of a device 10 according to the present invention is shown in FIGS. 6-8. The device comprises a housing 12 and a needle assembly 14 as described in relation to previous examples of the invention. The device 19 further comprises a force input mechanism 30, shown schematically in FIG. 10, a needle actuator 32, shown schematically in FIG. 11, and a deployment mechanism 26, shown in FIG. 12. The force input mechanism 30 and needle actuator 32 together form the excitation mechanism 28, shown schematically in FIG. 9. The excitation mechanism 28 is disposed substantially within the interior of the housing 12. The needle assembly 14 is disposed at one end within a shuttle 100, the operation of which will be described in further detail when the deployment mechanism 26 is discussed.

Figure 9:
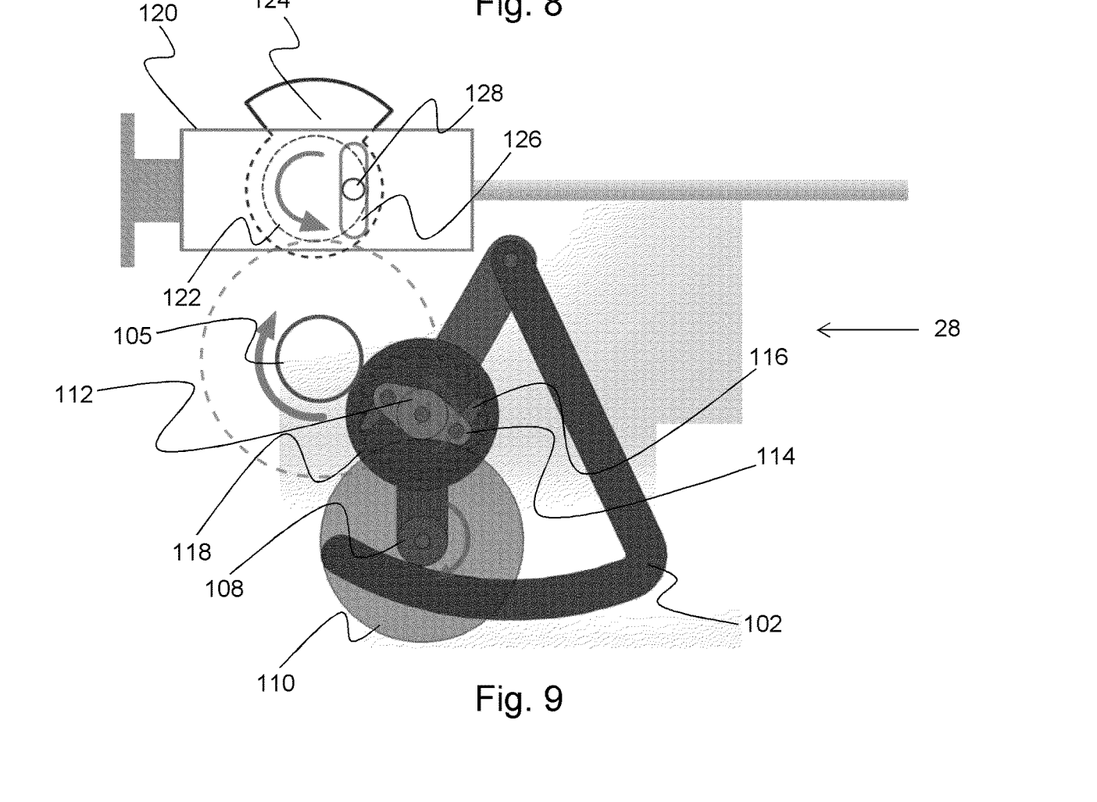
FIG. 9 is a schematic view of an excitation mechanism of the preferred embodiment of the present invention shown in FIG. 6.
Figure 10:
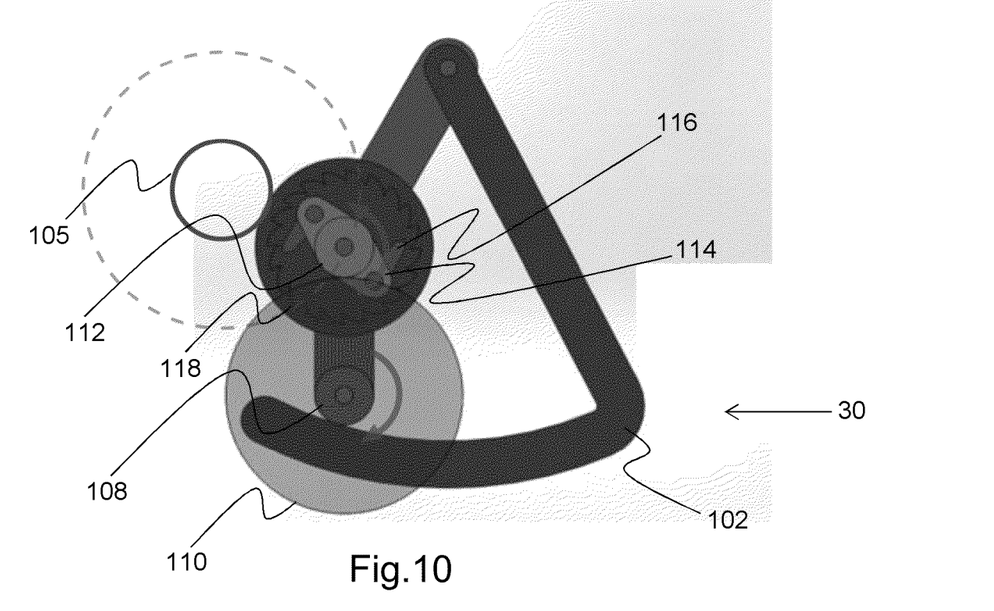
FIG. 10 is a schematic view of a force input mechanism of the excitation mechanism of FIG. 9.

The force input mechanism 30 is shown most clearly in FIGS. 7 and 8, and schematically in FIGS. 9 and 10, and comprises a trigger 102, a rack to pawl gear 104, a pawl assembly, a ratchet assembly 118, and an idler gear 105.

The trigger 102 is pivotably mounted to the housing 12, such that the trigger 102 is moveable relative to the housing upon operation by a user. A first portion of the trigger 102 is disposed outside of the housing 12 in a rest configuration, and a second portion of the trigger 102 is held inside of the housing 12 in a rest configuration. The trigger 102 comprises a rack 106 for engaging the rack to pawl gear 104. The rack 106 comprises a plurality of teeth disposed upon its length. The trigger further comprises a spring 103 fixedly mounted relative to the trigger 102 at the point where the trigger 102 is pivotably mounted to the housing 12.

The rack to pawl gear 104 comprises first and second concentrically formed toothed wheels 108, 110, and is centrally rotatably mounted within the housing 12. The first toothed wheel 108 has a substantially smaller diameter than the second toothed wheel 110, and the teeth of the first wheel 108 are shaped and dimensioned so as to engage the corresponding teeth of the rack 106. The teeth of the second toothed wheel 110 are shaped and dimensioned so as to engage the corresponding teeth of a pawl gear 112.

The pawl assembly comprises a pawl gear 112, an arm 114, and a plurality of pawls 116. The pawl gear 112 takes the form of a toothed wheel, and is rotatably mounted within the housing 12 such that the teeth of the pawl gear 112 are engaged with the teeth of the second toothed wheel 110 of the rack to pawl gear 104. The arm 114 is substantially elongate in form. A central region of the arm 114 is rotatably mounted to the housing 12, yet is fixedly mounted relative to the pawl gear 112, such that opposing ends of the arm 114 extend laterally outwardly from the pawl gear 112. Each end of the arm 114 comprises a pawl 116 that is pivotably mounted to the arm 114. Each pawl 116 is shaped and dimensioned so as to engage a corresponding tooth of a ratchet assembly 118 in an extended position.

The ratchet assembly 118 takes the form of a wheel comprising a first set of radially inwardly facing teeth for engaging a corresponding pawl 116 in its extended position, and a second set of radially outwardly facing teeth for engaging an idle gear 105, and corresponding portions of the needle actuator 32. The ratchet assembly 118 is rotatably mounted relative to the housing 12 about the same mounting point as the pawl gear 112, yet the wheel of the ratchet assembly 118 has a larger diameter than the diameter of the pawl assembly, such that the ratchet assembly 118 and the pawl assembly are substantially concentrically formed.

The idler gear 105 takes the form of a toothed wheel, and is rotatably mounted to the housing 12 such that the teeth 105 of the idler gear are engaged with the radially outwardly facing teeth of the ratchet assembly 118, and engaged with a corresponding portion of the needle actuator 32.

Figure 11:
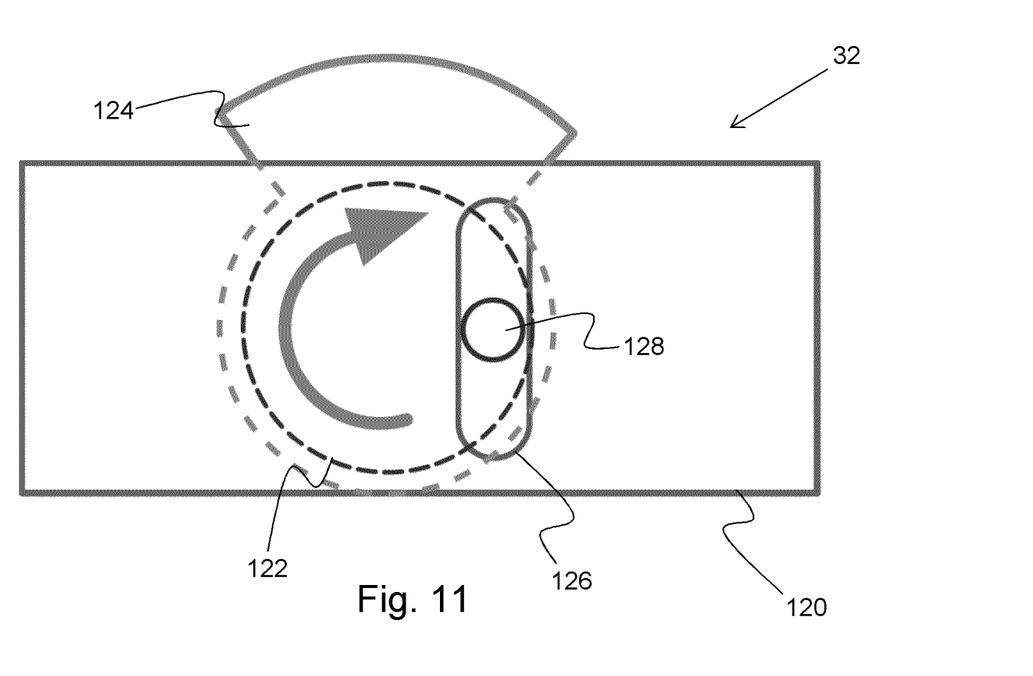
FIG. 11 is a schematic view of a needle actuator of the excitation mechanism of FIG. 9.

The needle actuator 32 is shown most clearly in FIGS. 7 and 8, and schematically in FIGS. 9 and 11, and comprises a shuttle casing 120, a drive gear 122, and an eccentric 124. The shuttle casing 120 is substantially elongate in form, and forms the outer housing of the shuttle 100 of the device 10, and is thus connected to the needle assembly 14. The shuttle casing 120 comprises a slot 126 for receiving a corresponding cam portion 128 of the drive gear 122. The slot 126 is substantially elongate in form, and extends transversely across substantially the entirety of the height of the shuttle casing 120.

The drive gear 122 comprises a toothed wheel and a cam portion. The drive gear 122 is rotatably mounted relative to the housing 12, such that the toothed wheel of the drive gear 122 engages the idler gear 105, and the cam portion 128 of the drive gear is mounted in the slot 126.

The eccentric 124 comprises a gear portion 130 that is rotatably mounted relative to the housing 12 such that the gear portion 130 is engaged with the radially outwardly facing teeth of the ratchet assembly 118. Thus, in the preferred embodiment of the present invention the eccentric 124 and the cam portion 128 are driven by separate gears, allowing the frequency of movement and vibration of the eccentric 124 and the cam portion 128 to be determined individually. Embodiments in which the eccentric 124 and the cam portion 128 are driven by the same gear are also envisaged.

In use, a user may depress the trigger 102 relative to the housing 12, thereby causing movement of the rack 106. The teeth of the rack 106 engage the first toothed wheel 108 of the rack to pawl gear 104, thereby causing rotation of the rack to pawl gear 104. The rotation of the rack to pawl gear 104 causes the second toothed wheel 110 to engage the pawl gear 112. Rotation of the pawl gear 112 drives rotational movement of the arm 114, which thereby causes the pawls 116 to move to an extended position, in which they engage the radially inwardly facing teeth of the ratchet assembly 118. This, in turn, drives the rotation of the idler gear 105 and the gear portion 130 of the eccentric 124, via engagement with the radially outwardly facing teeth of the ratchet assembly 118. The idler gear 105 drives the drive gear 122, which causes the cam portion 128 to rotate, and move within the slot 126 of the shuttle casing. As the motion of the cam portion 128 is constrained by the slot 126, the cam portion 128 contacts the edges of the slot 126, thus causing lateral motion of the shuttle casing 120. As the shuttle casing 120 is connected to the needle assembly 14, the motion of the shuttle casing 120 is thereby vibrationally transferred to the needle assembly 14. The rotational movement of the eccentric 124 via the gear portion 130, further adds a component of oscillatory motion to the needle assembly 14 that is substantially orthogonal to the motion provided by the cam portion 128.

The needle assembly 14 is thereby able to oscillate upon actuation of the trigger 102, and thus the echogenicity of the needle assembly 14 is altered relative to the surrounding tissue.

When the trigger 102 is released, the spring 103 acts to push the rack 106 in a reverse direction. This in turn causes the pawl gear 112 to rotate in a reverse direction, thus causing disengagement of the pawls 116 from the ratchet assembly 118, and movement of the pawls 116 to a retracted position. Whilst the pawls 116 are in the retracted position, the ratchet assembly 118, and its associated gear train as discussed above, continues to rotate in the original driven direction.

Figure 12:
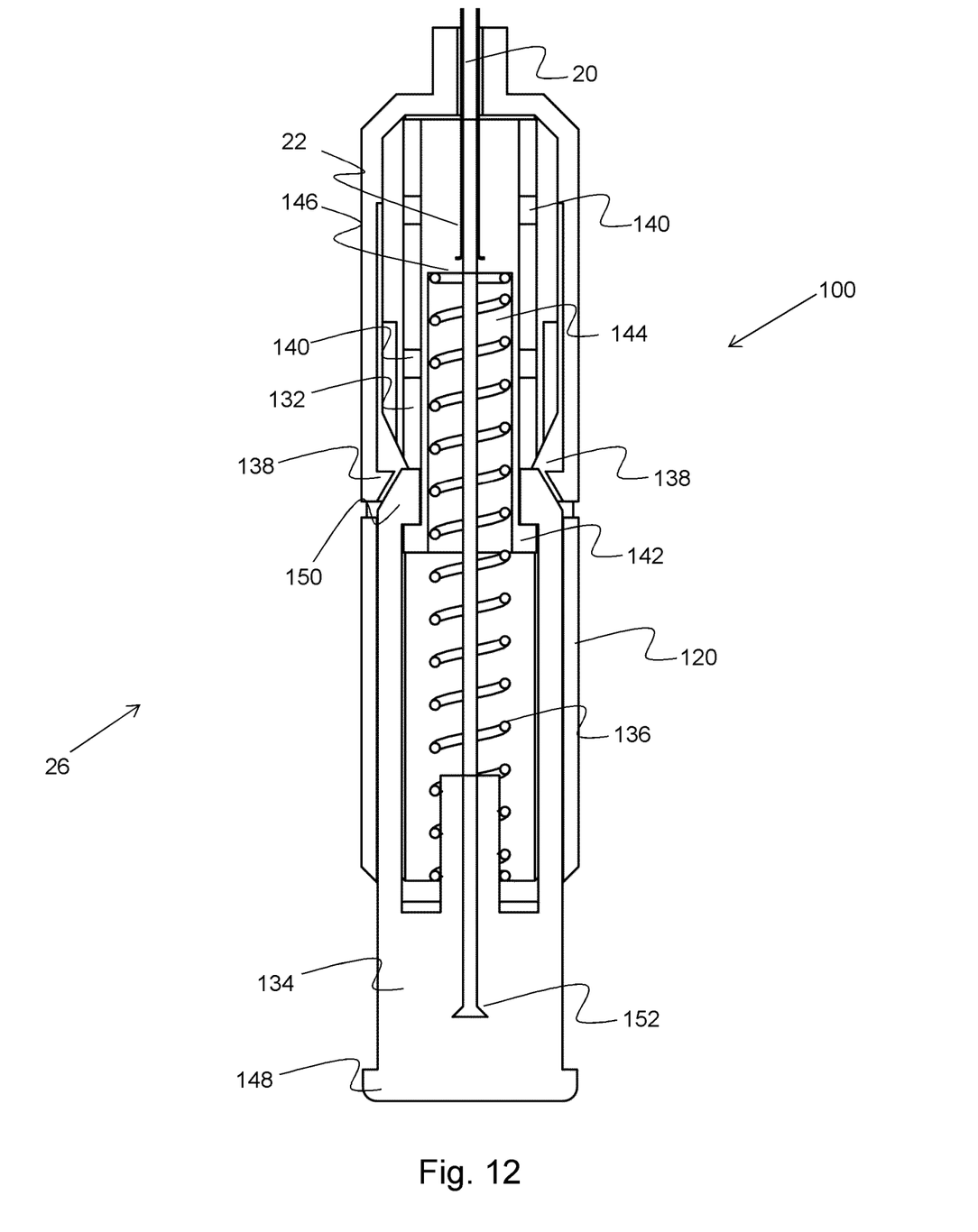
FIG. 12 is a sectional schematic view of a deployment mechanism of the device of FIG. 6 in a rest configuration.
Figure 13:
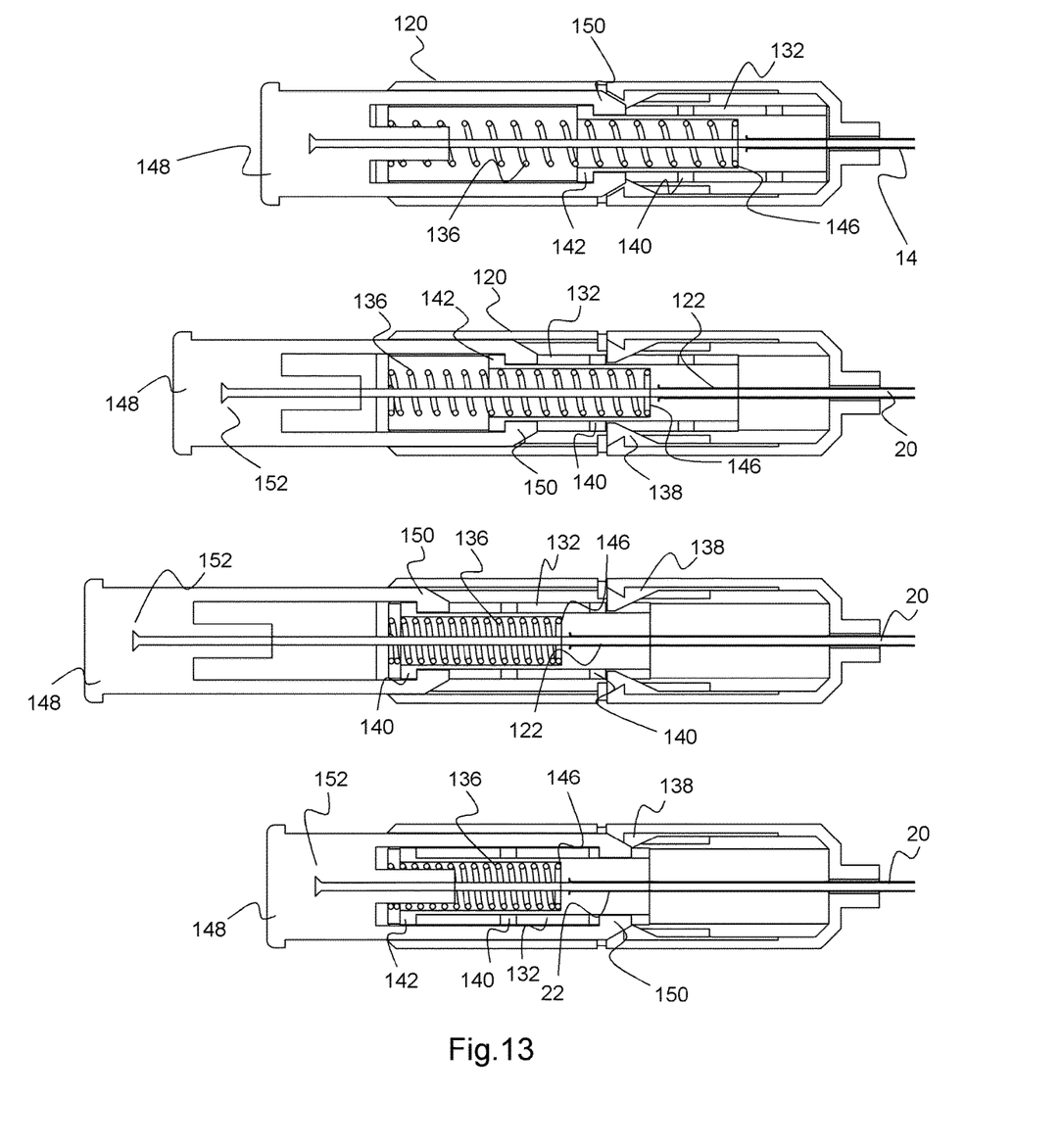
FIG. 13 shows schematic views of the deployment mechanism of FIG. 12 at different stages of operation.

A deployment mechanism 26 for use with the preferred embodiment of the present invention is shown in a rest configuration in FIG. 12, and in various stages of operation in FIG. 13. The deployment mechanism 26 comprises a shuttle casing 120, an inner slide 132, an actuation portion 134, and a spring 136.

The shuttle casing 120 is elongate in form, and is substantially hollow. An inner surface of the shuttle casing 120 comprises a plurality of latch formations 138 for releasably engaging corresponding projections 140 of the inner slide 132.

The inner slide 132 is slidably mounted within the shuttle casing 120. An outer surface of the inner slide 132 comprises a plurality of upstanding projections 140 and an engagement formation 142 for engaging a corresponding formation 150 of the actuation portion 134. The inner slide 132 further comprises a central hollow bore for receiving the needle assembly 14, and a chamber 144 for receiving the spring 136. The central hollow bore and the chamber 144 are in direct fluid communication, yet the central hollow bore has a much smaller diameter than the chamber 144, such that an abutment surface 146 is formed at the interface between the hollow central bore and the chamber 144. The sleeve 22 of the needle assembly 14 terminates, and is held by the inner slide 132, in a region of the abutment surface 146.

The actuation portion 134 comprises a grip formation 148 for a user to grasp, an engagement formation 150 for engaging a corresponding engagement formation 142 of the inner slide 132, and a needle retaining formation 152 for retaining the needle 20 of the needle assembly 14. The actuation portion 134 is elongate in form, and is mounted such that substantially the entirety of the actuation portion 134 is held within the shuttle casing 120, between the outer surface of the inner slide 132 and the inner surface of the shuttle casing 120. The needle retaining formation 152 holds a proximal end of the needle 20 such that it extends centrally through the chamber 144 and the hollow central bore of the inner slide 132, and thereby also through the sleeve 22.

The spring 136 is disposed between a proximal wall of the shuttle casing and the abutment surface 146 of the inner slide.

Various operational stages of the deployment mechanism are shown in FIG. 13. In use, the needle assembly may be inserted into a tissue. The grip formation 148 is grasped by a user, and pulled transversely backwards relative to a patient. The engagement formation 150 of the actuation portion 134, and the engagement formation 142 of the inner slide 132, contact each other, and the inner slide 132 is thus pulled towards the proximal wall of the shuttle casing 120. As the inner slide 132 moves towards the proximal wall of the shuttle casing 132, the spring 136 is compressed between the abutment surface 146 and the proximal wall of the shuttle casing 120. As the grip portion 148 is pulled, both the sleeve 22 and the needle 20 are pulled backwards, the former due to the motion of the inner slide 132, and the latter due to the motion of the needle retaining formation 152 of the actuation portion 134.

The grip formation 148 is pulled until a projection 140 of the inner slide 132 engages a latch formation 138 of the shuttle casing 120, thereby holding the inner slide 132 in place relative to the shuttle casing 120. The inner slide 132 may be moved further until a further projection 140 contacts a latch formation 138, if it is desired to take a larger sample from the desired tissue. In either circumstance, the inner slide 132, and thus the sleeve 22, is fixed relative to the shuttle casing 120.

The grip formation 148 may then be depressed in an opposing direction, and, due to the fixed nature of the needle 20 relative to the grip portion 148, the needle 20 extends outwardly from the sleeve 22 of the needle assembly at a distal end.

Once the grip portion 148 is depressed far enough, the engagement formations 150 of the actuation portion 134 will contact the latch formations 138 of the shuttle casing 120. Application of sufficient pressure to the grip portion 148 will cause the latch formations 138 to deform outwardly, and release the corresponding projection 140 of the inner slide 132. Thus, the inner slide 132 and the sleeve 22 will return rapidly to their rest configurations, the sleeve 22 covering the needle 20, and cut a desired sample from the tissue. The needle assembly 14 may then be removed from the tissue.

Figure 14:
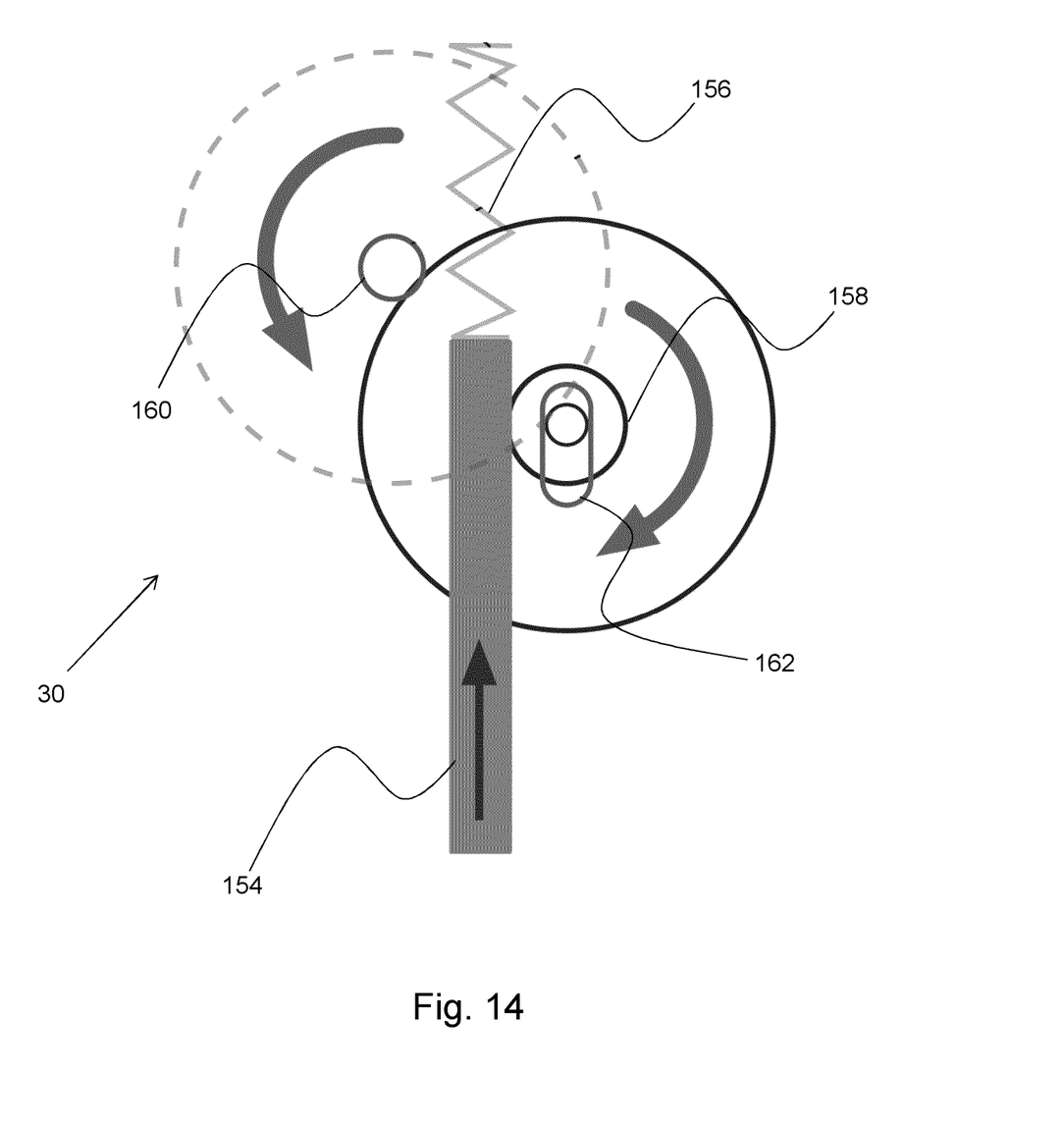
FIG. 14 is a schematic view of an alternative force input mechanism for the device of FIG. 6.

A schematic drawing of an alternative force input mechanism 30 for use with the device of FIG. 6 is shown in FIG. 14.

The force input mechanism 30 comprises a rack 154, a rack return spring 156, a drive gear 158, and a spur gear 160.

The rack 154 comprises a plurality of teeth for engaging a corresponding first set of teeth of the drive gear 158. The drive gear 158 comprises a second set of teeth for engaging a corresponding set of teeth of the spur gear 160. The drive gear 158 is mounted for linear movement relative to the shuttle casing 120, with its motion constrained by a slot 162.

When the rack 154 is actuated by a user in a forward direction, the teeth of the rack 154 engage the corresponding set of teeth of the drive gear 158. The forward motion of the rack 154 causes the drive gear 158 to rotate about its central axis. Furthermore, the forward motion of the rack 154 pushes the drive gear 158 along the slot 162, such that it engages the spur gear 160, and causes the spur gear 160 to rotate. The spur gear 160 thus drives the needle actuator 32.

When actuation of the rack 154 by the user is ceased, the spring 156 acts to push the rack 154 in a reverse direction. Thus, the rack 154 pulls the drive gear 158 in an opposing direction along the slot 162, such that it disengages the spur gear 160. The spur gear 160 continues to rotate, provided that there is sufficient energy contained within the system.

Figure 15:
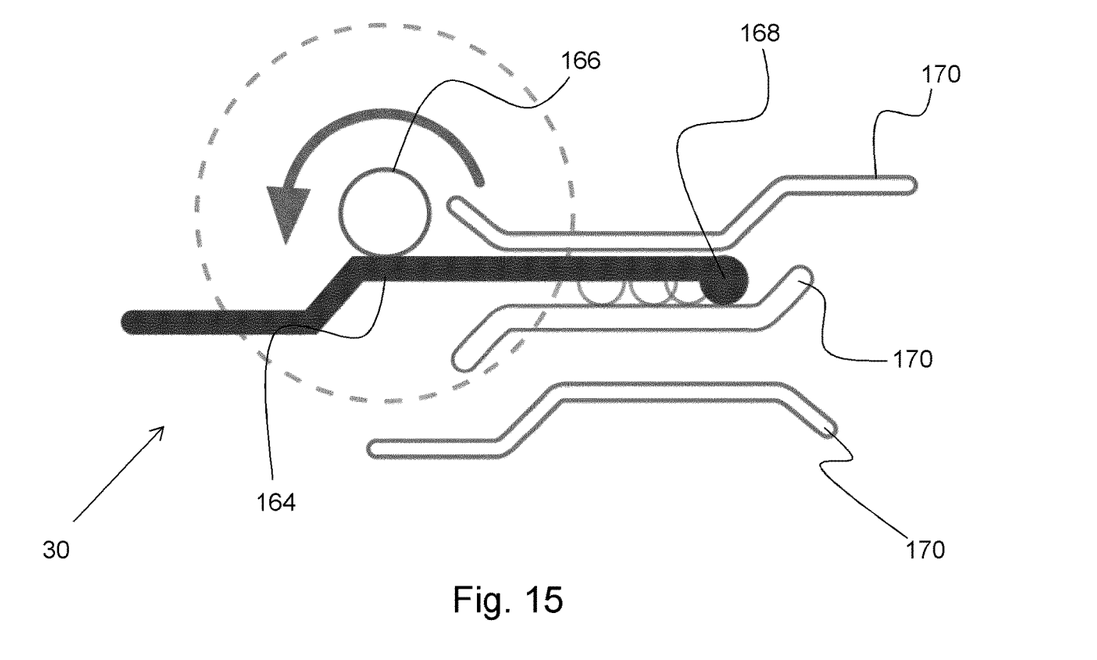
FIG. 15 is a schematic view of a further alternative force input mechanism for the device of FIG. 6.

A schematic of a further force input mechanism 30 for use with the device of FIG. 6 is shown in FIG. 15.

The force input mechanism 30 comprises a rack gear 164, a pinion gear 166, a pin 168, and a track 170. The rack gear 164 comprises teeth for engaging corresponding teeth of the pinion gear 166. The rack gear 164 is resiliently biased to its retracted position.

As the rack gear 164 is advanced in a forward direction, to an extended position, the teeth of the rack gear 164 engage the teeth of the pinion gear 166, and cause the pinion gear 166 to rotate in the direction indicated in FIG. 14. As the rack gear 164 is advanced, the pin 168 follows the track 170, until the rack gear 164 becomes disengaged as the pin 168 advances over a first lip of the track 170. The pinion gear 166 continues to rotate despite the disengagement of the rack gear 164. The pin 168 continues to follow the path of the track 170 as the resilient biasing of the rack gear 164 pushes the rack gear 164 back towards its original retracted position. The pin 168 advances over a second lip of the track 170 on its return journey, until the rack gear is back in its original retracted position.

In any of the above described embodiments, the input mechanism may be provided with a latch formation such that the input mechanism can be primed and latched prior to use of the device, such that the energy is stored, pending release of the latch mechanism. Alternatively, the input mechanism may directly transfer energy, eg from a user, to the needle actuator, and may release the needle actuator following transfer of energy to enable continued movement of the needle.

If the physician experiences difficulty in seeing the needle on the ultrasound display, the physician can actuate the input mechanism or release the latch, thereby causing vibration of the needle as and when desired. A latch may take the form of any stop member suitable to hold the input mechanism in a primed condition, whereby, when the stop member is displaced, the mechanism can move to drive movement of the actuator.

Furthermore, it will be appreciated by the skilled person that any of the manual input mechanisms described above may be replaced with an electrically driven mechanism. For example a conventional electric motor or solenoid may be used to generate a rotating or linear input for the excitation mechanism. Thus a battery may be used as the energy store for actuation of the mechanism rather than a spring or other mechanism. For example, rotation of the eccentric 52 of FIG. 2, actuator 56 of FIG. 3 or actuator 68 of FIG. 4 may be driven directly or indirectly by an electric motor instead of a rack and pinion arrangement. If a linear drive is required this may be achieved using a solenoid, rack-and-pinion driven by a motor or other conventional electric actuator.

In an electrically powered embodiment, the housing will have one or more buttons to allow operation of the excitation mechanism. A single button may be provided to cause operation of the mechanism for a predetermined duration of time, for example between 1 and 10 seconds, and preferably 2-5 seconds. Alternatively, a single button for the excitation mechanism may provide a start/stop toggle.

In use, the physician can insert the needle assembly 14 in the usual manner into the body and may track the location of the needle assembly using ultrasound imaging. In the event that the needle assembly becomes difficult to view on the ultrasound display, the physician can actuate the excitation mechanism so that the needle assembly becomes more readily visible in the display.

In either a manual or an electrically-powered embodiment, mechanism(s) described above (i.e. any or any combination of the input, excitement and/or deployment mechanisms) may be retained within the housing, or a portion thereof, for reuse and the needle assembly and other associated parts of the device may be disposed of. For example the mechanism may be disposed in a first housing portion which may be removably attachable to a second housing portion which holds the needle assembly. Thus the needle assembly can be removed after use and the first housing portion can be retained for re-use with a new needle assembly attached thereto. In one such embodiment, the battery and electrical components of an electrically powered device may be contained in the first housing portion. A two-part needle device may be provided in which the needle or needle assembly clips into the housing. It is also feasible that the battery and some electrical components could be retained whilst the mechanism(s) for actuation the needle assembly could be disposed of with the needle.

Alternatively, and particularly in the case of a manually actuated device, the entire device may be disposable after use.

All of the embodiments described above allow excitation of the needle assembly without inhibiting the deployment of the needle assembly to take a tissue sample in use. In any of the above-described embodiments, the amplitude of the vibrations experienced by the needle are sufficiently small relative to the dimensions of the needle itself to avoid significant displacement of the needle or damage to tissue through which the needle passes. Furthermore the level of vibration is not sufficient to cause any substantial discomfort or distress to a patient.

The invention claimed is:

1. A medical needle location device comprising:
a housing arranged to be gripped by a user and
a needle supported by the housing, the needle depending from the housing towards a needle tip,
wherein the housing comprises an excitation mechanism for applying an oscillatory motion to the needle during location within a human or animal body, and the device comprises a drive mechanism for driving the excitation mechanism,
the drive mechanism comprising a user interface portion adapted to receive mechanical energy input from the user, the excitation mechanism being mechanically coupled to the drive mechanism such that the drive mechanism and the excitation mechanism are manually driven, the excitation mechanism is configured to apply the oscillatory motion to the needle at a frequency greater than a frequency of operation of the drive mechanism by the user interface portion, wherein the device further comprises a needle deployment mechanism for gross longitudinal or rotational movement of the needle.

2. A device according to claim 1, wherein the excitation mechanism comprises an excitation member arranged to impart cyclical excitation forces to the needle.

3. A device according to claim 2, wherein the excitation member is rotatable.

4. A device according to claim 3, wherein the rotatable excitation member comprises an eccentric member.

5. A device according to claim 3, wherein the rotatable excitation member comprises one or more projections or teeth thereon arranged to interfere with a receiving member.

6. A device according to claim 2 comprising an intermediate member in a force path between the excitation member and the needle.

7. A device according to claim 1, wherein the drive mechanism is adapted to receive energy from an energy store, which is charged by the moveable user interface portion being coupled directly, or via intermediate members, to the energy store.

8. A device according to claim 1, wherein the user interface portion is moveable relative to the housing of the device.

9. A device according to claim 8, wherein the user interface portion is moveable towards a portion of the housing of the device during actuation.

10. A device according to claim 1, wherein the drive mechanism imparts motion to an excitation member of the excitation mechanism arranged to impart cyclical excitation forces to the needle.

11. A device according to claim 10, wherein the drive mechanism comprises a release mechanism for disengaging the drive mechanism from the excitation member.

12. A device according to claim 11, wherein the release mechanism comprises a resilient member.

13. A device according to claim 10, wherein the drive mechanism comprises a drive member actuable between a first configuration in which the drive member is engaged with the excitation member, and a second configuration in which the drive member is disengaged from the excitation member.

14. A device according to claim 13, wherein the excitation member is configured to maintain the motion imparted on the excitation member by the drive mechanism when the drive mechanism is in the second configuration.

15. A device according to claim 1, wherein the excitation mechanism is arranged to cause excitation of the needle for a duration of one second or more.

16. A device according to claim 15, wherein the mechanism excites the needle for a predetermined duration of a plurality of seconds.

17. A device according to claim 1, wherein the excitation mechanism imparts vibrations to the needle.

18. A device according to claim 1, wherein the device is a biopsy needle device for taking tissue samples from a body.

19. A device according to claim 1, wherein the excitation and deployment mechanisms are individually operable or triggered.

20. A device according to claim 1, wherein the needle is surrounded by a sleeve.

21. A device according to claim 1, wherein the excitation mechanism applies the oscillatory motion to the needle at a frequency greater than 5 Hz.

* * * * *